United States Patent [19]

Fischer

[11] 3,933,464
[45] Jan. 20, 1976

[54] HERBICIDE
[75] Inventor: Adolf Fischer, Mutterstadt, Germany
[73] Assignee: BASF Aktiengesellschaft, Ludwigshafen Germany
[22] Filed: May 23, 1974
[21] Appl. No.: 472,653

Related U.S. Application Data
[62] Division of Ser. No. 348,085, April 4, 1973.

[30] Foreign Application Priority Data
Apr. 13, 1972 Germany.............................. 2217698

[52] U.S. Cl.......................................... 71/92; 71/88
[51] Int. Cl.²............................................ A01N 9/22
[58] Field of Search.................................. 71/88, 92

[56] References Cited
UNITED STATES PATENTS

| | | | |
|---|---|---|---|
| 3,235,363 | 2/1966 | Luckenbaugh et al. | 71/92 |
| 3,436,207 | 4/1969 | Soboczenski | 71/92 |
| 3,689,507 | 9/1972 | Gates et al. | 71/88 |
| 3,758,477 | 9/1973 | Zeidler et al. | 71/92 |

Primary Examiner—Lewis Gotts
Assistant Examiner—Catherine L. Mills
Attorney, Agent, or Firm—Johnston, Keil, Thompson & Shurtleff

[57] ABSTRACT

New and valuable herbicide mixtures of 2-ethoxy-2,3-dihydro-3,3-dimethyl-5-benzofuranylmethane sulfonate and 3-cyclohexyl-5,6-trimethylene uracil, optionally 1-substituted by acetyl, propionyl or α,α-dimethyl-β-acetoxypropionyl.

2 Claims, No Drawings

HERBICIDE

RELATED APPLICATION

This application is a division of my copending application Ser. No. 348,085, filed Apr. 4, 1973, the disclosure of which is incorporated herein by reference.

The present invention relates to a herbicide comprising a composition of 2-ethoxy-2,3-dihydro-3,3-dimethyl-5-benzofuranylmethane sulfonate and a uracil.

It is known to use methane sulfonates, pyridazones, uracils and carbamates for controlling broadleaved and grassy weeds. However, their action is poor.

I have now found that a composition of
a. a compound of the formula

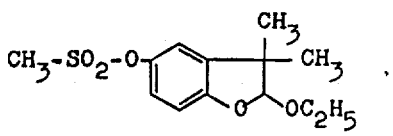

and
b. a compound of the formula

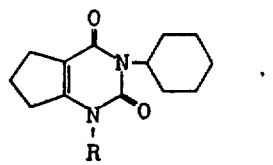

wherein R denotes hydrogen, acetyl, propionyl or α,α-dimethyl-β-acetoxypropionyl, has a good herbicidal action.

The active ingredients may be mixed in any ratio; it is however preferred to employ a ratio (by weight) of a : b of from 5 : 1 to 1 : 5, preferably 3 : 1 to 1 : 3.

The agents according to the invention may be used as solutions, emulsions, suspensions, oil dispersion, granules or dusts. The form of application depends entirely on the purpose for which the agents are being used; in any case it should ensure a fine distribution of the active ingredient.

For the preparation of solutions to be sprayed direct, mineral oil fractions of medium to high boiling point, such as kerosene or diesel oil, further coal-tar oils and oils of vegetable or mineral origin, and cyclic hydrocarbons such as tetrahydronaphthalene and alkylated naphthalenes are suitable.

Aqueous formulations may be prepared from emulsion concentrates, pastes or wettable powders by adding water. To prepare emulsions the ingredients as such or dissolved in a solvent may be homogenized in water or organic solvents by means of wetting or dispersing agents, e.g., polyethylene oxide adducts. Concentrates which are suitable for dilution with water may be prepared from active ingredient, wetting agent, adherent, emulsifying or dispersing agent and possibly solvent.

Oils of various types may be added to ready-to-use spray liquors.

Dusts may be prepared by mixing or grinding the active ingredients with a solid carrier, e.g., kieselguhr, talc, clay or fertilizers.

Granules may be prepared by bonding the active ingredients to solid carriers.

Directly sprayable dispersions may also be prepared with oils.

The new compounds may be mixed with fertilizers, insecticides, fungicides and other herbicides.

The new herbicides may be applied either pre- or postemergence, and are particularly suited for controlling dicotyledonous seed weeds and monocotyledonous seed grasses in crops such as beet, spinach, potatoes, peas, beans and groundnuts.

EXAMPLE 1

In the greenhouse, seeds of beet (Beta vulgaris), common lambsquarters (Chenopodium album), wild mustard (Sinapis arvensis), slender foxtail (Alopecurus myosuroides) and wild oat (Avena fatua) were sown in loamy sandy soil and subsequently treated with the following amounts of the following active ingredients and compositions thereof, each active ingredient and each composition being emulsified or dispersed in 500 liters of water per hectare: 500

I. 2-ethoxy-2,3-dihydro-3,3-dimethyl-5-benzofuranylmethane sulfonate, 1.5 2 and 3 kg/hectare;

II 1-(α,α-dimethyl-β-acetoxypropionyl)-3-cyclohexyl-5,6-trimethylene uracil, 1.5 and 3 kg/hectare;

III 3-cyclohexyl-5,6-trimethylene uracil, 1.5 and 3 kg/hectare;

I + II: 1.5 + 1.5 kg/hectare;
I + III: 1.5 + 1.5 kg/hectare.

The following results show that the compositions have a better herbicidal action than their individual components, combined with good crop plant compatibility.

| Active ingredient kg/ha | I 1.5 | 2 | 3 | II 1.5 | 3 | III 1.5 | 3 | I+II 1.5+1.5 | I+III 1.5+1.5 |
|---|---|---|---|---|---|---|---|---|---|
| Beta vulgaris | 5 | 10 | 20 | 0 | 30 | 0 | 40 | 5 | 5 |
| Chenopodium album | 20 | 30 | 40 | 45 | 90 | 35 | 90 | 95 | 85 |
| Sinapis arvensis | 15 | 20 | 35 | 50 | 95 | 40 | 100 | 95 | 80 |
| Alopecurus myosuroides | 65 | 85 | 100 | 30 | 75 | 25 | 75 | 100 | 100 |
| Avena fatua | 60 | 80 | 100 | 25 | 55 | 20 | 70 | 100 | 95 |

0 = no damage
100 = complete destruction

EXAMPLE 2

The plants beet (Beta vulgaris), common lambsquarters (Chenopodium album), chamomile (Matricaria chamomilla), wild mustard (Sinapis arvensis), slender foxtail (Alopecurus myosuroides), and annual bluegrass (Poa annua) were treated at a growth height of 3 to 13 cm with the following amounts of the following active ingredients and compositions thereof, each active ingredient and each composition being emulsified or dispersed in 500 liters of water per hectare:

I 2-ethoxy-2,3-dihydro-3,3-dimethyl-5-benzofuranylmethane sulfonate, 0.5 1, 1.5, 2and 3 kg/hectare;

II 3-methoxycarbonylaminophenyl-N-3'-methylphenyl)-carbamate, -methylphenyl)-carbamate, 1 and 2 kg per hectare;

III 1-phenyl-4-amino-5-chlorpyridazone-(6), 2 and 3 kg per hectare;

IV 1-phenyl-4-(α-hydroxy-βββ-trichloroethyl-amino-5-bromopyridazone-(6), 1.5 and 2 kg/hectare;

1-(αα-dimethyl-β-acetoxypropionyl)-3-cyclohexyl-5,6-trimethylene uracil, 0.5 and 2 kg/hectare;

VI 3-cyclohexyl-5,6-trimethylene uracil, 1 and 2 kg/hectare;

I + II: 1 + 1 kg/hectare;
I + III: 1 + 2 kg/hectare;
I + IV: 0.5 + 1.5 kg/hectare;
I + V: 1.5 + 0.5 kg/hectare;
I + VI: 1 + 1 kg/hectare.

After 2 to 3 weeks it was ascertained that the compositions had a better herbicidal action than their individual components, combined with good crop plant compatibility.

The results are given below:

| Active ingredient kg/ha | I | | | | | II | | III | | IV | |
|---|---|---|---|---|---|---|---|---|---|---|---|
| | 0.5 | 1 | 1.5 | 2 | 3 | 1 | 2 | 2 | 3 | 1.5 | 2 |
| Beta vulgaris | 0 | 0 | 5 | 20 | 30 | 0 | 20 | 0 | 0 | 0 | 0 |
| Chenopodium album | 10 | 20 | 35 | 50 | 70 | 80 | 100 | 65 | 90 | 60 | 85 |
| Matricaria chamomilla | 20 | 30 | 50 | 70 | 90 | 35 | 80 | 60 | 90 | 65 | 90 |
| Sinapis arvensis | 10 | 20 | 40 | 60 | 90 | 75 | 100 | 50 | 85 | 60 | 80 |
| Alopecurus myosuroides | 30 | 50 | 60 | 100 | 100 | 10 | 15 | 40 | 80 | 40 | 50 |
| Poa annua | 25 | 45 | 55 | 90 | 100 | 10 | 20 | 35 | 75 | 45 | 60 |

| Active ingredient kg/ha | V | | VI | | I+II 1+1 | I+III 1+2 | I+IV 0.5+1-.5 | I+V 1.5+0.5 | I+VI 1+1 |
|---|---|---|---|---|---|---|---|---|---|
| | 0.5 | 2 | 1 | 2 | | | | | |
| Beta vulgaris | 0 | 20 | 5 | 25 | 0 | 0 | 0 | 5 | 5 |
| Chenopodium album | 30 | 100 | 50 | 100 | 100 | 100 | 100 | 95 | 95 |
| Matricaria chamomilla | 35 | 95 | 40 | 90 | 100 | 100 | 95 | 100 | 100 |
| Sinapis arvensis | 40 | 100 | 65 | 100 | 100 | 100 | 100 | 100 | 100 |
| Alopecurus myosuroides | 25 | 95 | 45 | 90 | 90 | 100 | 95 | 100 | 100 |
| Poa annua | 30 | 100 | 45 | 90 | 85 | 95 | 90 | 100 | 100 |

0 = no damage
100 = complete destruction

EXAMPLE 3

In the greenhouse various plants were treated at a growth height of from 3 to 11 cm with the following amounts of the following individual active ingredients and compositions thereof as oil dispersions:

I 2-ethoxy-2,3-dihydro-3,3-dimethyl-5-benzofuranyl-methanesulfonate, 0.25, 0.5, 0.75 and 1.0. kg/ha;

II 1-phenyl-4-amino-5-chlorpyridazone-(6)-0.25, 0.5, 0.75 and 1.0 kg/ha;

III 3-cyclohexyl-5,6-trimethylene uracil, 0.25 0.5, 0.75 and 1.0 kg/ha;

I + II: 0.25 + 0.25, 0.25 + 0.75 and 0.75 + 0.25 kg/ha;

I + III: 0.25 + 0.25, 0.25 + 0.75 and 0.75 + 0.25 kg/ha.

After 2 to 3 weeks it was ascertained that the compositions had a better herbicidal action than their individual components, combined with the same good crop plant compatibility.

The results of this experiment are given below:

| Active ingredient kg/ha | I | | | |
|---|---|---|---|---|
| | 0.25 | 0.5 | 0.75 | 1.0 |
| Crop plants: | | | | |
| Beta vulgaris | 0 | 0 | 0 | 0 |
| Unwanted plants: | | | | |
| Avena fatua | 18 | 30 | 40 | 55 |
| Bromus tectorum | 30 | 35 | 43 | 60 |
| Matricaria chamomilla | 15 | 23 | 27 | 34 |
| Setaria faberii | 33 | 49 | 55 | 60 |
| Sinapis arvensis | 8 | 15 | 20 | 24 |

0 = no damage
100 = complete destruction

| Active ingredient kg/ha | II | | | |
|---|---|---|---|---|
| | 0.25 | 0.5 | 0.75 | 1.0 |
| Crop plants: | | | | |
| Beta vulgaris | 0 | 0 | 0 | 0 |
| Unwanted plants: | | | | |
| Avena fatua | 7 | 11 | 13 | 15 |
| Bromus tectorum | 5 | 10 | 16 | 25 |
| Matricaria chamomilla | 15 | 35 | 40 | 45 |
| Setaria faberii | 8 | 11 | 15 | 25 |
| Sinapis arvensis | 23 | 34 | 38 | 40 |

0 = no damage
100 = complete destruction

| Active ingredient kg/ha | III | | | |
|---|---|---|---|---|
| | 0.25 | 0.5 | 0.75 | 1.0 |
| Crop plants: | | | | |
| Beta vulgaris | 0 | 0 | 0 | 0 |
| Unwanted plants: | | | | |
| Avena fatua | 10 | 15 | 25 | 35 |
| Bromus tectorum | 15 | 25 | 30 | 40 |
| Matricaria chamomilla | 15 | 24 | 35 | 45 |
| Setaria faberii | 20 | 24 | 30 | 40 |
| Sinapis arvensis | 25 | 35 | 40 | 70 |

0 = no damage
100 = complete destruction

| Active ingredient kg/ha | I + II | | |
|---|---|---|---|
| | 0.25+0.75 | 0.25+0.25 | 0.75+0.25 |
| Crop plants: | | | |
| Beta vulgaris | 0 | 0 | 0 |
| Unwanted plants: | | | |
| Avena fatua | 70 | 60 | 75 |
| Bromus tectorum | 85 | 60 | 70 |
| Matricaria chamomilla | 85 | 62 | 77 |
| Setaria faberii | 72 | 70 | 75 |
| Sinapis arvensis | 80 | 60 | 80 |

0 = no damage
100 = complete destruction

| Active ingredient kg/ha | I + III | | |
|---|---|---|---|
| | 0.25+0.75 | 0.25+0.25 | 0.75+0.25 |
| Crop plants: | | | |
| Beta vulgaris | 0 | 0 | 0 |
| Unwanted plants: | | | |
| Avena fatua | 75 | 60 | 82 |
| Bromus tectorum | 80 | 80 | 85 |
| Matricaria chamomilla | 76 | 62 | 72 |
| Setaria faberii | 80 | 83 | 95 |
| Sinapis arvensis | 80 | 65 | 80 |

0 = no damage
100 = complete destruction

EXAMPLE 4

In the greenhouse various plants were treated at a growth height of from 2 to 11 cm with the following amounts of the following individual active ingredients and compositions thereof as pastes:

I  2-ethoxy-2,3-dihydro-3,3-dimethyl-5-benzo furnanylmethanesulfonate, 0.15, 0.25, 0.5, 0.75, 1.0, 1.25, 1.5, 1.65, 2.0, 3.0 and 4.0 kg/ha;

II  1-phenyl-4-amino-5-chlorpyridazone-(6), 0.15 0.25, 0.5, 0.75, 1.0, 1.25, 1.5, 1.65, 2.0, 3.0 and 4.0 kg/ha;

III  3-cyclohexyl-5,6-trimethylene uracil, 0.15, 0.25, 0.5, 0.75, 1.0, 1.25, 1.5, 1.65, 2.0, 3.0 and 4.0 kg/ha;

IV  N-(4-bromophenyl)-N'-methoxy-N'-methylurea, 3 and 4 kg/ha;

I + II  0.25+0.75, 0.25+0.25, 0.75+0.25, 0.5+0.5, 0.25+1.25, 1.25+0.25, 0.75+0.75, 1.5+0.15, 0.15+1.5, 3.0+1.0, 1.0+1.0 and 1.0+3.0 kg/ha;

I + III  0.25+0.75, 0.25+0.25, 0.75+0.25, 0.5+0.5, 0.25+1.25, 1.25+0.25, 0.75+0.75, 1.5+0.15, 0.15+1.5, 3.0+1.0, 1.0+1.0 and 1.0+3.0 kg/ha;

I + IV  1.0+3.0 kg/ha.

After 2 to 3 weeks it was ascertained that compositions I + II and I + III had a better herbicidal action than the individual ingredients I, II and III combined with the same good crop plant compatibility, and better crop plant compatibility than active ingredients IV and the composition I + IV.

The results are given below:

| Active ingredient kg/ha | 0.15 | 0.25 | 0.5 | 0.75 | 1.0 | 1.25 | 1.5 | 1.65 | 2.0 | 3.0 | 4.0 |
|---|---|---|---|---|---|---|---|---|---|---|---|
| Crop plants: | | | | | | | | | | | |
| Beta vulgaris | 0 | 0 | 0 | 0 | 0 | 0 | 5 | 10 | 20 | 30 | 35 |
| Unwanted plants: | | | | | | | | | | | |
| Avena fatua | 10 | 15 | 25 | 35 | 50 | 60 | 60 | 65 | 70 | 80 | 100 |
| Bromus tectorum | 15 | 25 | 30 | 40 | 55 | 58 | 63 | 64 | 75 | 80 | 100 |
| Matricaria chamomilla | 5 | 10 | 20 | 23 | 30 | 35 | 50 | 60 | 70 | 90 | 100 |
| Setaria faberii | 10 | 30 | 35 | 45 | 55 | 60 | 70 | 70 | 90 | 100 | 100 |
| Sinapis arvensis | 3 | 5 | 10 | 15 | 20 | 28 | 40 | 50 | 60 | 90 | 100 |

0 = no damage
100 = complete destruction

| Active ingredient kg/ha | 0.15 | 0.25 | 0.5 | 0.75 | 1.0 | 1.25 | 1.5 | 1.65 | 2.0 | 3.0 | 4.0 |
|---|---|---|---|---|---|---|---|---|---|---|---|
| Crop plants: | | | | | | | | | | | |
| Beta vulgaris | 0 | 0 | 0 | 0 | 0 | 0 | 0 | 0 | 0 | 0 | 10 |
| Unwanted plants: | | | | | | | | | | | |
| Avena fatua | 1 | 3 | 5 | 8 | 10 | 12 | 15 | 18 | 25 | 30 | 45 |
| Bromus tectorum | 0 | 5 | 11 | 15 | 20 | 22 | 28 | 29 | 30 | 35 | 70 |
| Matricaria chamomilla | 7 | 10 | 30 | 35 | 40 | 45 | 50 | 52 | 60 | 90 | 100 |
| Setaria faberii | 1 | 3 | 8 | 10 | 20 | 25 | 30 | 30 | 33 | 40 | 50 |
| Sinapis arvensis | 15 | 20 | 30 | 33 | 35 | 40 | 44 | 45 | 50 | 85 | 100 |

0 = no damage
100 = complete destruction

| Active ingredient kg/ha | III 0.15 | 0.25 | 0.5 | 0.75 | 1.0 | 1.25 | 1.5 | 1.65 | 2.0 | 3.0 | 4.0 | IV 3.0 | 4.0 |
|---|---|---|---|---|---|---|---|---|---|---|---|---|---|
| Crop plants: | | | | | | | | | | | | | |
| Beta vulgaris | 0 | 0 | 0 | 0 | 0 | 0 | 5 | 10 | 25 | 30 | 50 | 100 | 100 |
| Unwanted plants: | | | | | | | | | | | | | |
| Avena fatua | 3 | 5 | 10 | 20 | 30 | 35 | 45 | 60 | 75 | 85 | 100 | 100 | 100 |
| Bromus tectorum | 5 | 10 | 20 | 25 | 35 | 40 | 50 | 60 | 75 | 90 | 100 | 100 | 100 |
| Matricaria chamomilla | 5 | 10 | 20 | 30 | 40 | 45 | 60 | 75 | 90 | 100 | 100 | 100 | 100 |
| Setaria faberii | 5 | 15 | 20 | 25 | 35 | 40 | 55 | 60 | 70 | 80 | 90 | 100 | 100 |
| Sinapis arvensis | 15 | 20 | 30 | 35 | 65 | 75 | 85 | 90 | 100 | 100 | 100 | 100 | 100 |

0 = no damage
100 = complete destruction

| Active ingredient kg/ha | I + II 0.25+0.75 | 0.25+0.25 | 0.75+0.25 | 0.5+0.5 | 0.25+1.25 | 1.25+0.25 |
|---|---|---|---|---|---|---|
| Crop plants: | | | | | | |
| Beta vulgaris | 0 | 0 | 0 | 0 | 0 | 0 |
| Unwanted plants: | | | | | | |
| Avena fatua | 65 | 40 | 70 | 65 | 75 | 90 |
| Bromus tectorum | 75 | 50 | 75 | 73 | 85 | 93 |
| Matricaria chamomilla | 70 | 45 | 60 | 70 | 80 | 70 |
| Setaria faberii | 75 | 55 | 75 | 65 | 90 | 93 |
| Sinapis arvensis | 70 | 50 | 70 | 60 | 70 | 65 |

0 = no damage
100 = complete destruction

| Active ingredient kg/ha | I + II 0.75 + 0.75 | 1.5+0.15 | 0.15+1.5 |
|---|---|---|---|
| Crop plants: | | | |
| Beta vulgaris | 0 | 5 | 0 |
| Unwanted plants: | | | |
| Avena fatua | 80 | 90 | 85 |
| Bromus tectorum | 78 | 85 | 80 |
| Matricaria chamomilla | 80 | 85 | 95 |
| Setaria faberii | 85 | 100 | 90 |
| Sinapis arvensis | 72 | 80 | 70 |

0 = no damage
100 = complete destruction

| Active ingredient kg/ha | I + II | | | | I + III | | |
|---|---|---|---|---|---|---|---|
| | 3.0+1.0 | 1.0+1.0 | 1.0+3.0 | 0.25+0.75 | 0.25+0.25 | 0.75+0.25 | 0.5+0.5 |
| Crop plants: | | | | | | | |
| Beta vulgaris | 30 | 0 | 0 | 0 | 0 | 0 | 0 |
| Unwanted plants: | | | | | | | |
| Avena fatua | 100 | 100 | 100 | 70 | 50 | 65 | 65 |
| Bromus tectorum | 100 | 90 | 100 | 75 | 55 | 70 | 75 |
| Matricaria chamomilla | 100 | 95 | 100 | 60 | 45 | 55 | 60 |
| Setaria faberii | 100 | 95 | 100 | 80 | 65 | 85 | 75 |
| Sinapis arvensis | 100 | 95 | 100 | 90 | 50 | 70 | 80 |

0 = no damage
100 = complete destruction

| Active ingredient kg/ha | I + III | | | | |
|---|---|---|---|---|---|
| | 0.25+1.25 | 1.25+0.25 | 0.75+0.75 | 1.5+1.5 | 0.15+1.5 |
| Crop plants: | | | | | |
| Beta vulgaris | 0 | 0 | 0 | 5 | 5 |
| Unwanted plants: | | | | | |
| Avena fatua | 82 | 90 | 80 | 100 | 85 |
| Bromus tectorum | 90 | 88 | 85 | 95 | 90 |
| Matricaria chamomilla | 80 | 85 | 83 | 100 | 95 |
| Setaria faberii | 95 | 90 | 95 | 100 | 100 |
| Sinapis arvensis | 96 | 94 | 100 | 100 | 100 |

0 = no damage
100 = complete destruction

| Active ingredient kg/ha | I + III | | | I + IV |
|---|---|---|---|---|
| | 3.0+1.0 | 1.0+1.0 | 1.0+3.0 | 1.0+3.0 |
| Crop plants: | | | | |
| Beta vulgaris | 30 | 0 | 30 | 100 |
| Unwanted plants: | | | | |
| Avena fatua | 100 | 95 | 100 | 100 |
| Bromus tectorum | 100 | 100 | 100 | 100 |
| Matricaria chamomilla | 100 | 100 | 100 | 100 |
| Setaria faberii | 100 | 100 | 100 | 100 |
| Sinapis arvensis | 100 | 100 | 100 | 100 |

0 = no damage
100 = complete destruction

EXAMPLE 5

An agricultural plot was sown with the seeds of various plants. The soil prepared in this manner was then immediately treated with the following amounts of the following individual active ingredients and compositions thereof as dispersions or emulsions:

I 2-ethoxy-2,3-dihydro-3,3-dimethyl-5-benzofuranylmethane sulfonate 0.15 0.25, 0.5, 0.75, 1.0, 1.25, 1.5, 1.65, 2.0, 3.0 and 4.0 kg/ha;

II 1-phenyl-4-amino-5-chlorpyridazone-(6) 0.15 0.25, 0.5, 0.75, 1.0, 1.25, 1.5, 1.65, 2.0, 3.0 and 4.0 kg/ha;

III 3-cyclohexyl-5,6-trimethylene uracil 0.15, 0.25, 0.5, 0.75, 1.0, 1.25, 1.5, 1.65, 2.0, 3.0 and 4.0 kg/ha;

IV N-(4-bromophenyl)-N'-methoxy-N'-methylurea 3 and 4 kg/ha;

I + II 0.25+0.75, 0.25+0.25, 0.75+0.25, 0.5+0.5, 0.25+1.25, 1.25+0.25, 0.75+0.75, 1.5+0.15, 0.15+1.5, 3.0+1.0, 1.0, 1.0+3.0 kg/ha;

I + III 0.25+0.75, 0.25+0.25, 0.75+0.25, 0.5+0.5, 0.25+1.25, 1.25+0.25, 0.75+0.75, 1.5+0.15, 0.15+1.5, 3.0+1.0, 1.0+1.0 and 1.0+3.0 kg/ha;

I + IV 1.0+3.0 kg/ha.

After 3 to 4 weeks it was ascertained that compositions I + II and I+ III had a better herbicidal action than the individual active ingredients I, II and III combined with the same good crop plant compatibility, and better crop plant compatibility than active ingredient IV and the composition I + IV.

The results are given below:

| Active ingredient kg/ha | I | | | | | | | | | | |
|---|---|---|---|---|---|---|---|---|---|---|---|
| | 0.15 | 0.25 | 0.5 | 0.75 | 1.0 | 1.25 | 1.5 | 1.65 | 2.0 | 3.0 | 4.0 |
| Crop plants: | | | | | | | | | | | |
| Beta vulgaris | 0 | 0 | 0 | 0 | 0 | 2 | 5 | 6 | 10 | 20 | 30 |
| Unwanted plants: | | | | | | | | | | | |
| Avena fatua | 2 | 5 | 16 | 21 | 40 | 50 | 60 | 65 | 80 | 100 | 100 |

-continued

I

| Active ingredient kg/ha | 0.15 | 0.25 | 0.5 | 0.75 | 1.0 | 1.25 | 1.5 | 1.65 | 2.0 | 3.0 | 4.0 |
|---|---|---|---|---|---|---|---|---|---|---|---|
| Bromus tectorum | 3 | 5 | 14 | 18 | 25 | 30 | 35 | 37 | 50 | 70 | 100 |
| Matricaria chamomilla | 6 | 10 | 20 | 30 | 40 | 45 | 50 | 53 | 70 | 90 | 100 |
| Setaria faberii | 11 | 20 | 30 | 40 | 50 | 60 | 75 | 80 | 90 | 100 | 100 |
| Sinapis arvensis | 0 | 0 | 5 | 5 | 10 | 13 | 18 | 19 | 20 | 35 | 50 |

0 = no damage
100 = complete destruction

II

| Active ingredient kg/ha | 0.15 | 0.25 | 0.5 | 0.75 | 1.0 | 1.25 | 1.5 | 1.65 | 2.0 | 3.0 | 4.0 |
|---|---|---|---|---|---|---|---|---|---|---|---|
| Crop plants: | | | | | | | | | | | |
| Beta vulgaris | 0 | 0 | 0 | 0 | 0 | 0 | 0 | 0 | 0 | 0 | 15 |
| Unwanted plants: | | | | | | | | | | | |
| Avena fatua | 0 | 0 | 2 | 5 | 6 | 8 | 15 | 15 | 18 | 20 | 30 |
| Bromus tectorum | 0 | 0 | 5 | 7 | 10 | 13 | 15 | 17 | 22 | 30 | 35 |
| Matricaria chamomilla | 7 | 8 | 10 | 18 | 25 | 30 | 45 | 47 | 60 | 90 | 100 |
| Setaria faberii | 4 | 6 | 10 | 14 | 20 | 25 | 35 | 37 | 40 | 60 | 65 |
| Sinapis arvensis | 10 | 15 | 20 | 25 | 30 | 35 | 50 | 55 | 60 | 70 | 80 |

0 = no damage
100 = complete destruction

III

| Active ingredient kg/ha | 0.15 | 0.25 | 0.5 | 0.75 | 1.0 | 1.25 | 1.5 | 1.65 | 2.0 | 3.0 | 4.0 |
|---|---|---|---|---|---|---|---|---|---|---|---|
| Crop plants: | | | | | | | | | | | |
| Beta vulgaris | 0 | 0 | 0 | 0 | 0 | 0 | 0 | 0 | 10 | 40 | 50 |
| Unwanted plants: | | | | | | | | | | | |
| Avena fatua | 3 | 5 | 10 | 15 | 18 | 20 | 23 | 25 | 50 | 70 | 95 |
| Bromus tectorum | 12 | 18 | 25 | 35 | 40 | 50 | 60 | 65 | 75 | 100 | 100 |
| Matricaria chamomilla | 10 | 20 | 40 | 56 | 70 | 80 | 85 | 90 | 100 | 100 | 100 |
| Setaria faberii | 10 | 15 | 25 | 34 | 40 | 46 | 55 | 60 | 70 | 75 | 83 |
| Sinapis arvensis | 7 | 10 | 20 | 30 | 35 | 38 | 43 | 50 | 70 | 100 | 100 |

0 = no damage
100 = complete destruction

IV

| Active ingredient kg/ha | 3.0 | 4.0 |
|---|---|---|
| Crop plants: | | |
| Beta vulgaris | 100 | 100 |
| Unwanted plants: | | |
| Avena fatua | 100 | 100 |
| Bromus tectorum | 100 | 100 |
| Matricaria chamomilla | 100 | 100 |
| Setaria faberii | 80 | 100 |
| Sinapis arvensis | 100 | 100 |

0 = no damage
100 = complete destruction

I + II

| Active ingredient kg/ha | 0.25+0.75 | 0.25+0.25 | 0.75+0.25 | 0.5+0.5 | 0.25+1.25 | 1.25+0.25 |
|---|---|---|---|---|---|---|
| Crop plants: | | | | | | |
| Beta vulgaris | 0 | 0 | 0 | 0 | 0 | 2 |
| Unwanted plants: | | | | | | |
| Avena fatua | 45 | 30 | 55 | 45 | 90 | 95 |
| Bromus tectorum | 50 | 26 | 52 | 50 | 55 | 70 |
| Matricaria chamomilla | 80 | 50 | 70 | 82 | 85 | 80 |
| Setaria faberii | 85 | 70 | 70 | 65 | 90 | 95 |
| Sinapis arvenis | 55 | 40 | 50 | 53 | 80 | 75 |

0 = no damage
100 = complete destruction

I + II

| Active ingredients kg/ha | 0.75+0.75 | 1.5+0.15 | 0.15+1.5 | 3.0+1.0 | 1.0+1.0 | 1.0+3.0 |
|---|---|---|---|---|---|---|
| Crop plants: | | | | | | |
| Beta vulgaris | 0 | 5 | 0 | 20 | 0 | 0 |
| Unwanted plants: | | | | | | |
| Avena fatua | 85 | 80 | 70 | 100 | 95 | 100 |
| Bromus tectorum | 72 | 55 | 50 | 100 | 75 | 100 |
| Matricaria chamomilla | 88 | 80 | 75 | 100 | 95 | 100 |
| Setaria faberii | 85 | 97 | 92 | 100 | 100 | 100 |
| Sinapis arvensis | 82 | 70 | 80 | 95 | 85 | 100 |

0 = no damage

| Active ingredients kg/ha | 0.75+0.75 | 1.5+0.15 | I + II 0.15+1.5 | 3.0+1.0 | 1.0+1.0 | 1.0+3.0 |
|---|---|---|---|---|---|---|

100 = complete destruction

| Active ingredients kg/ha | 0.25+0.75 | 0.25+0.25 | I + III 0.75+0.25 | 0.5+0.5 | 0.25+1.25 | 1.25+0.25 |
|---|---|---|---|---|---|---|
| Crop plants: | | | | | | |
| Beta vulgaris | 0 | 0 | 0 | 0 | 0 | 2 |
| Unwanted plants: | | | | | | |
| Avena fatua | 50 | 30 | 55 | 56 | 70 | 85 |
| Bromus tectorum | 70 | 52 | 68 | 70 | 80 | 85 |
| Matricaria chamomilla | 85 | 60 | 80 | 83 | 100 | 100 |
| Setaria faberii | 83 | 65 | 85 | 86 | 90 | 95 |
| Sinapis arvensis | 60 | 35 | 50 | 55 | 75 | 80 |

0 = no damage
100 = complete destruction

| Active ingredients kg/ha | 0.75+0.75 | 1.5+0.15 | I + III 0.15+1.5 | 3.0+1.0 | 1.0+1.0 | 1.0+3.0 | I + IV 1.0+3.0 |
|---|---|---|---|---|---|---|---|
| Crop plants: | | | | | | | |
| Beta vulgaris | 0 | 5 | 0 | 20 | 0 | 40 | 100 |
| Unwanted plants: | | | | | | | |
| Avena fatua | 80 | 90 | 80 | 100 | 95 | 100 | 100 |
| Bromus tectorum | 80 | 90 | 85 | 100 | 95 | 100 | 100 |
| Matricaria chamomilla | 100 | 100 | 100 | 100 | 100 | 100 | 100 |
| Setaria faberii | 92 | 95 | 100 | 100 | 100 | 100 | 100 |
| Sinapis arvensis | 76 | 75 | 70 | 95 | 70 | 100 | 100 |

0 = no damage
100 = complete destruction

EXAMPLE 6

An agricultural plot was sown with the seeds of various plants. The soil prepared in this manner was then immediately treated with the following amounts of the following active ingredients and compositions thereof in the form of granules:

I   2-ethoxy-2,3-dihydro-3,3-dimethyl-5-benzofuranylmethane sulfonate, 0.25, 0.5, 0.75 and 1.0 kg/ha;
II  1-phenyl-4-amino-5-chloropyridazone-(6), 0.25 0.5, 0.75 and 1.0 kg/ha;
III 3-cyclohexyl-5,6-trimethylene uracil, 0.25, 0.5, 0.75 and 1.0 kg/ha;
I + II: 0.25+0.25, 0.25+0.75 and 0.75+0.25 kg/ha
I + III: 0.25+0.25, 0.25+0.75 and 0.75+0.25 kg/ha.

After 2 to 3 weeks it was ascertained tha the compositions had a better herbicidal action than their individual components, combined with the same good crop plant compatibility.

The results are given below:

| Active ingredients kg/ha | I 0.25 | 0.5 | 0.75 | 1.0 | II 0.25 | 0.5 | 0.75 | 1.0 | III 0.25 | 0.5 | 0.75 | 1.0 |
|---|---|---|---|---|---|---|---|---|---|---|---|---|
| Crop plants: | | | | | | | | | | | | |
| Beta vulgaris | 0 | 0 | 0 | 0 | 0 | 0 | 0 | 0 | 0 | 0 | 0 | 0 |
| Unwanted plants: | | | | | | | | | | | | |
| Avena fatua | 5 | 16 | 21 | 40 | 0 | 2 | 5 | 6 | 5 | 10 | 15 | 18 |
| Bromus tectorum | 5 | 14 | 18 | 25 | 0 | 5 | 7 | 10 | 18 | 25 | 35 | 40 |
| Matricaria chamomilla | 10 | 20 | 30 | 40 | 8 | 10 | 18 | 25 | 20 | 40 | 56 | 70 |
| Setaria faberii | 20 | 30 | 40 | 50 | 6 | 10 | 14 | 20 | 15 | 25 | 34 | 40 |
| Sinapis arvensis | 0 | 5 | 5 | 10 | 15 | 20 | 25 | 30 | 10 | 20 | 30 | 35 |

0 = no damage
100 = complete destruction

| Active ingredient kg/ha | I + II 0.25+0.75 | 0.25+0.25 | 0.75+0.25 | 0.25+0.75 | I + III 0.25+0.25 | 0.75+0.25 |
|---|---|---|---|---|---|---|
| Crop plants: | | | | | | |
| Beta vulgaris | 0 | 0 | 0 | 0 | 0 | 0 |
| Unwatend plants: | | | | | | |
| Avena fatua | 45 | 30 | 55 | 50 | 30 | 55 |
| Bromus tectorum | 50 | 26 | 52 | 70 | 52 | 68 |
| Matricaria chamomilla | 80 | 50 | 70 | 85 | 60 | 80 |
| Setaria faberii | 85 | 7L | 70 | 83 | 65 | 85 |
| Sinapis arvensis | 55 | 40 | 50 | 60 | 35 | 50 |

0 = no damage
100 = complete destruction

I claim:

1. A herbicide composition containing a herbicidally effective amount of a mixture consisting essentially of (a) 2-ethoxy-2,3-dihydro-3,3-dimethyl-5-benzofuranylmethane sulfonate and (b) 3-cyclohexyl-5,6-trimethylene uracil in a weight ratio of $a$ to $b$ in the range of 5:1 to 1:5.

2. A herbicide composition containing a herbicidally effective amount of a mixture consisting essentially of (a) 2-ethoxy-2,3-dihydro-3,3-dimethyl-5-benzofuranylmethane sulfonate and (b) 1-($\alpha,\alpha$-dimethyl-$\beta$-acetoxypropionyl)-3-cyclohexyl-5,6-trimethylene uracil in a weight ratio of $a$ to $b$ in the range of 1:1 to 3:1.

* * * * *